US012345683B2

(12) United States Patent
Lu et al.

(10) Patent No.: US 12,345,683 B2
(45) Date of Patent: Jul. 1, 2025

(54) METHODS FOR DETERMINING THE YOUNG'S MODULUS OF A CEMENTITIOUS MATERIAL

(71) Applicant: Purdue Research Foundation, West Lafayette, IN (US)

(72) Inventors: Na Lu, West Lafayette, IN (US); Zhihao Kong, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 220 days.

(21) Appl. No.: 18/002,789

(22) PCT Filed: Jul. 1, 2021

(86) PCT No.: PCT/US2021/040067
§ 371 (c)(1),
(2) Date: Dec. 21, 2022

(87) PCT Pub. No.: WO2022/006383
PCT Pub. Date: Jan. 6, 2022

(65) Prior Publication Data
US 2023/0243781 A1    Aug. 3, 2023

Related U.S. Application Data

(60) Provisional application No. 63/062,998, filed on Aug. 7, 2020, provisional application No. 63/047,771, filed on Jul. 2, 2020.

(51) Int. Cl.
*G01N 29/12*    (2006.01)
*G01N 29/24*    (2006.01)
(Continued)

(52) U.S. Cl.
CPC ......... *G01N 29/12* (2013.01); *G01N 29/2437* (2013.01); *G01N 29/2475* (2013.01);
(Continued)

(58) Field of Classification Search
CPC ............... G01N 29/12; G01N 29/2437; G01N 29/2475; G01N 29/4418; G01N 2291/014;
(Continued)

(56) References Cited

U.S. PATENT DOCUMENTS 5,741,971 A *  4/1998  Lacy ...................... G01N 29/32
                                                        73/152.16
7,987,728 B2    8/2011  Song et al.
(Continued)

FOREIGN PATENT DOCUMENTS

CA        3099005 A1 * 11/2019 ......... B28B 23/0031
CN      101535844 A  *  9/2009 ........... G01N 23/005
(Continued)

OTHER PUBLICATIONS

Chen et al., "Piezoelectric-Ceramic-Embedded Smart Concrete Module for Structure Health Monitory", IEEE Sensors, 2009, pp. 453-458 (Year: 2009).*

(Continued)

*Primary Examiner* — David L Singer
(74) *Attorney, Agent, or Firm* — Hartman Global IP Law; Gary M. Hartman; Domenica N. S. Hartman

(57) ABSTRACT

A method includes filling a cavity of a form defined by one or more boundaries with an uncured concrete mixture such that the uncured concrete mixture contacts or envelops a piezoelectric sensor within the form, receiving one or more electrical signals from the piezoelectric sensor as the uncured concrete mixture cures within the form to define a concrete sample, determining an electrical signal-frequency spectrum of the electrical signal(s) received from the piezoelectric sensor, determining one or more resonant frequencies of the concrete sample based on the electrical signal-frequency spectrum, determining a Young's modulus of the (Continued)

concrete sample based on the one or more resonant frequencies thereof, and outputting the determined Young's modulus or information based on the determined Young's modulus.

20 Claims, 6 Drawing Sheets

(51) Int. Cl.
    *G01N 29/44*     (2006.01)
    *G01N 29/46*     (2006.01)
    *G01N 33/38*     (2006.01)

(52) U.S. Cl.
    CPC ......... *G01N 29/4418* (2013.01); *G01N 29/46* (2013.01); *G01N 33/383* (2013.01); *G01N 2291/014* (2013.01); *G01N 2291/0232* (2013.01); *G01N 2291/0251* (2013.01); *G01N 2291/02827* (2013.01)

(58) Field of Classification Search
    CPC ... G01N 2291/0232; G01N 2291/0251; G01N 29/46; G01N 33/383; G01N 2291/02827
    USPC .......................................................... 73/579
    See application file for complete search history.

(56) References Cited

U.S. PATENT DOCUMENTS

| | | | | |
|---|---|---|---|---|
| 2007/0046289 A1* | 3/2007 | Troxler | ............... | G01N 23/203 |
| | | | | 324/334 |
| 2011/0083503 A1* | 4/2011 | Iverson | ............... | G01N 33/383 |
| | | | | 73/290 V |
| 2015/0309007 A1* | 10/2015 | Bellotti | ............... | G01N 29/348 |
| | | | | 73/597 |

FOREIGN PATENT DOCUMENTS

| | | | | | |
|---|---|---|---|---|---|
| CN | 105527013 | A | * | 4/2016 | ............ G01H 11/08 |
| JP | 2010266378 | A | * | 11/2010 | |
| KR | 20120004164 | A | * | 1/2012 | |
| KR | 101184048 | | | 9/2012 | |
| KR | 20120126559 | | | 11/2012 | |
| KR | 101221684 | | | 1/2013 | |
| KR | 101645622 | B1 | * | 8/2016 | ........... G01N 33/383 |

OTHER PUBLICATIONS

Machine translation of JP 2010266378 A (Year: 2010).*
Machine Translation of KR 10-2012-0004164 (Year: 2012).*
Kim et al., "Artificial Neural Network-Based Early-Age Concrete Strength Monitoring Using Dynamic Response Signals", Sensors, Jun. 7, 2017, pp. 1-12 (Year: 2017).*
Huo et al., "Dynamic Modelling of Embeddable Piezoceramic Transducers", Sensors, Dec. 5, 2017, pp. 1-21 (Year: 2017).*
Chen et al., "Advances in the Structural Health Monitoring of Bridges Using Piezoelectric Transducers", Sensors, Dec. 7, 2018, pp. 1-24 (Year: 2018).*
Tareen et al., "Comparative Analysis and Strength Estimation of Fresh Concrete Based on Ultrasonic Wave Propagation and Maturity Using Smart Temperature and PZT Sensors", Micromachines, Aug. 23, 2019, pp. 1-17 (Year: 2019).*
Kim et al, Artificial Neural Network-Based Early-Age Concrete Strength Monitoring Using Dynamic Response Signals, Sensors 2017, 17, 1319 (Year: 2017).*
Qin et al, Acoustic Emission Behavior of Early Age Concrete Monitored by Embedded Sensors, Materials 2014, 7, 6908-6918; doi: 10.3390/ma7106908 (Year: 2014).*
Tareen et al, Comparative Analysis and Strength Estimation of Fresh Concrete Based on Ultrasonic Wave Propagation and Maturity Using Smart Temperature and PZT Sensors, Published: Aug. 23, 2019 (Year: 2019).*
Zhu et al, Study on Piezoelectric Wave Propagation based Nondestructive Monitoring Method of Concrete, 2001 IEEE (Year: 2011).*
Ghafari et al, Evaluation the compressive strength of the cement paste blended with supplementary cementitious materials using a piezoelectric-based sensor, Construction and Building Materials 171 (2018) 504-510 (Year: 2018).*
Kocheria, A. et al., "Embedded Electrical Impediance-Based PZT Sensor for Monitoring Hydrating Concrete: Development and Evaluation", Smart Mater. Struct. 29 (2020) pp. 1-17.
International Preliminary Report on Patentability for International Application No. PCT/US2021/040067, dated Jan. 12, 2023, (6 pages).
Kocherla, A., et al., "Embedded Smart PZT-Based Sensor for Internal Damage Detection in Concrete Under Applied Compression", Measurement 163 (2020) 15 pages.
Kolluru, S.V. et al., "Determining Elastic Properties of Concrete Using Vibrational Resonance Frequencies of Standard Test Cylinders", Cement, Concrete, and Aggregates, CCAGDP, vol. 22, No. 2, Dec. 2000, pp. 81-89.
International Search Report & Written Opinion for International Application No. PCT/US2021/040067, dated Oct. 21, 2021, (10 pages).
Kim, Junkyeong, et al., "Early-Age Concrete Strength Estimation Based on Piezoelectric Sensor Using Artificial Neural Network", Prof. of SPIE vol. 9063, (7 pages).
Kolluru, S.V. et al., "Determining Elastic Properties of Concrete Using Vibrational Resonance Frequencies of Standard Test Cylinders", Cement, Concrete, and Aggregates, CCAGDP, vol. 22, (2000), pp. 81-89.
Narayanan, A. et al., "Embedded PZT Sensor for Monitoring Mechanical Inpedance of Hydrating Cementitious Materials", J Nondestruct Eval, vol. 36, No. 4, (2017), pp. 1-13.
Extended European Search Report for European Application No. 21832053.9, dated Jul. 4, 2024, 8 pages.

* cited by examiner

METHODS FOR DETERMINING THE YOUNG'S MODULUS OF A CEMENTITIOUS MATERIAL

CROSS REFERENCE TO RELATED APPLICATIONS

This application claims priority to International Patent Application No. PCT/US2021/40067 filed Jul. 1, 2021, which claims the benefit of U.S. Provisional Application Nos. 63/062,998 filed Aug. 7, 2020, and 63/047,771 filed Jul. 2, 2020. The contents of these prior patent documents are incorporated herein by reference.

BACKGROUND OF THE INVENTION

The present invention generally relates to material property testing of cementitious materials. The invention particularly relates to methods for measuring and/or monitoring material properties of a cementitious material during the curing thereof using one or more piezoelectric sensors.

The stress-strain relationship of concrete in its elastic stage (i.e., the Young's modulus) can be used to assess the performance of a given concrete mixture. A conventional method to determine the Young's modulus of a concrete mixture is a cylinder compressive test presented in ASTM C469, wherein strain and stress of a concrete cylinder are explicitly measured. However, this test requires the use of specific instruments which can be tedious to use.

As an alternative to physical concrete testing techniques, electromechanical impedance (EMI) methods may be used for in situ nondestructive testing (NDT) for concrete material property testing (e.g., strength and Young's modulus). EMI methods utilize sensor(s) that include a piezoelectric material, such as lead zirconide titanite (PZT) or quartz, that convert mechanical vibration within the concrete material into an AC current. Inversion algorithms may then be used to extract mechanical properties of the concrete material from electrical characteristics of the sensor(s).

However, existing EMI methods for Young's modulus testing are generally reliant on a correlation of EMI spectrum to conventional compressive testing. The statistical metrics used for the correlation may be capable of tracking the development of Young's modulus while concrete is hydrating but are not capable of quantitively determining the Young's modulus without referring to a reference state. EMI physical models usually consider the contribution of host structure as mechanical impedance which is more localized than global mechanical properties of the structure. Limited information is currently disclosed in the literature regarding the link between mechanical impedance and Young's modulus. Furthermore, literature in the art has determined that the EMI spectrum is highly sensitive to the boundary condition of sensors which results in poor repeatability due to sensor variability.

In view of the above, it can be appreciated that there are certain problems, shortcomings or disadvantages associated with the prior art, and that it would be desirable if methods were available for testing the Young's modulus of cementitious materials via electromechanical impedance without referring to a reference state and/or that accommodates for sensor variability.

BRIEF DESCRIPTION OF THE INVENTION

The present invention provides methods suitable for testing the Young's modulus of cementitious materials via electromechanical impedance without referring to a reference state and/or accommodating for sensor variability.

According to one aspect of the invention, a method is provided that includes filling a cavity of a form defined by one or more boundaries with an uncured concrete mixture such that the uncured concrete mixture contacts or envelops a piezoelectric sensor within the form, receiving one or more electrical signals from the piezoelectric sensor as the uncured concrete mixture cures within the form to define a concrete sample, determining an electrical signal-frequency spectrum of the electrical signal(s) received from the piezoelectric sensor, determining one or more resonant frequencies of the concrete sample based on the electrical signal-frequency spectrum, determining a Young's modulus of the concrete sample based on the one or more resonant frequencies thereof, and outputting the determined Young's modulus or information based on the determined Young's modulus.

Technical effects of the method described above preferably include the ability to nondestructively determine the Young's modulus or other material properties of a cementitious material in a reliable and efficient manner.

Other aspects and advantages of this invention will be appreciated from the following detailed description.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION OF THE INVENTION

Figure 2:
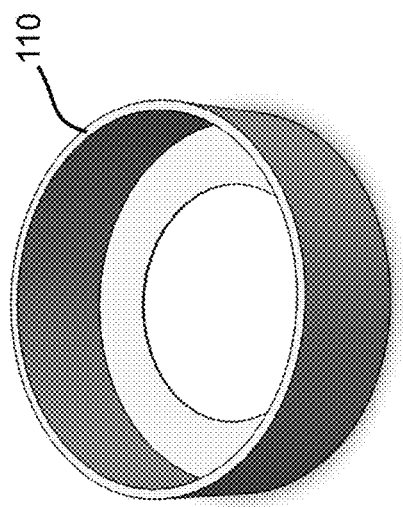
FIG. 2 represents a nonlimiting receptacle for use with the system of FIG. 1.

The intended purpose of the following detailed description of the invention and the phraseology and terminology employed therein is to describe what is shown in the drawings, which include the depiction of one or more nonlimiting embodiments of the invention, and to describe certain but not all aspects of what is depicted in the drawings, including the embodiment(s) depicted in the drawings. The following detailed description also describes certain investigations relating to the embodiments depicted in the drawings, and identifies certain but not all alternatives of the embodiment(s) depicted in the drawings. Therefore, the appended claims, and not the detailed description, are intended to particularly point out subject matter regarded as the invention, including certain but not necessarily all of the aspects and alternatives described in the detailed description.

Disclosed herein are methods of performing nondestructive, material property testing of cementitious materials or other curable materials with electromechanical testing systems. The method generally includes locating at least one piezoelectric (PZT) sensor within or in intimate contact with a volume of an uncured material and using the sensor to determine and/or monitor mechanical properties of the material as the material cures (e.g., during the hydration period of cement concrete).

In certain embodiments, the electromechanical testing system, including the piezoelectric sensor, is capable of continuously monitoring the mechanical properties of the material during the curing process to provide real-time sensing of changes in the properties of the material over a period of time. A particular but nonlimiting material property that may be determined and/or monitored by the system is the Young's modulus of the material.

For convenience, aspects of the invention are discussed herein primarily in relation to cementitious materials, particularly cement concrete. However, it should be understood that the principles disclosed herein are applicable to other non-cementitious materials such as but not limited to non-cementitious concretes such as various asphalt concretes and polymer concretes.

In the examples discussed herein, the sensor is within or in intimate contact with a volume of an uncured concrete mixture. As used herein, the term "uncured concrete mixture(s)" refers to fresh, uncured cementitious material mixtures, uncured cementitious material mixtures, or simply uncured cementitious materials that include a slurry composition of cementitious materials capable of sufficient fluid flow to be poured into and fill or partially fill the cavity of the form and thereafter cure into a solid cementitious body having a shape defined by one or more boundaries that define the form. An exemplary but not limiting uncured concrete mixture suitable for use with the system is a fluid slurry mixture of Portland cement, aggregate, and water. Such mixture may further include other additives such as pozzolans and/or superplasticizers. Other materials may be located within the form including reinforcing materials (e.g., rebar).

Figure 1:
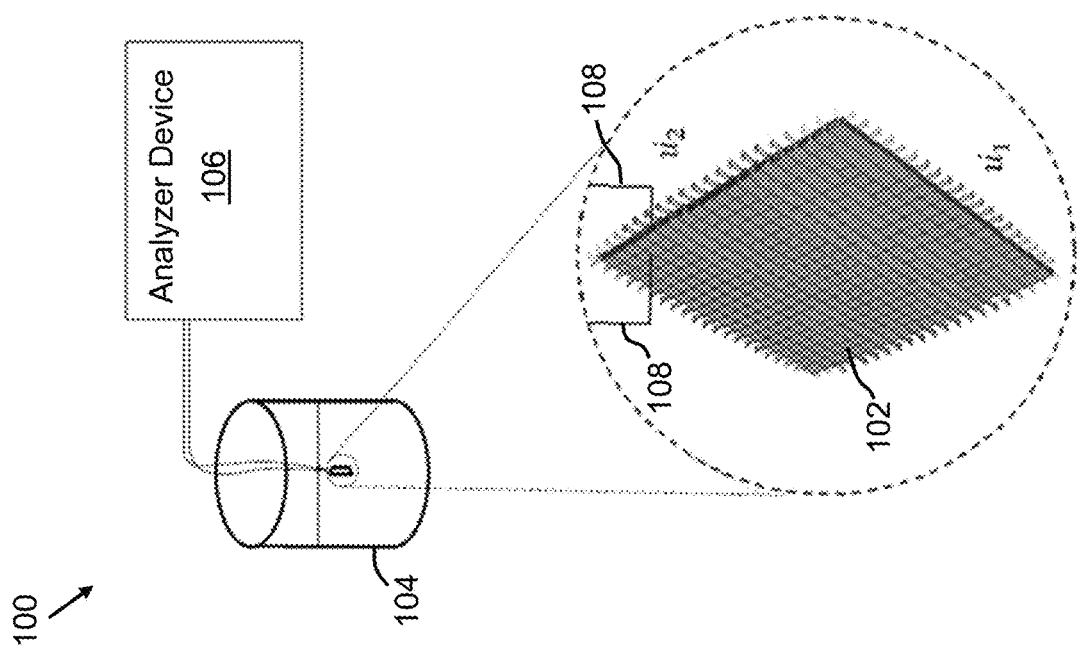
FIG. 1 represents a system in accordance with certain nonlimiting aspects of the invention.

FIG. 1 represents a first nonlimiting example of a system 100 suitable for use in performing nondestructive, material property testing of cementitious materials. In this example, the system 100 includes at least one piezoelectric (PZT) sensor 102, a form 104, and an analyzer device 106. As will become apparent from the following discussion, the analyzer device 106 may be of any suitable type capable of at least partially processing and analyzing outputs of the PZT sensor 102.

The PZT sensor 102 includes a piezoelectric material that produces an electric charge in response to application of mechanical stress thereto. Electrical charges produced by the sensor 102 may be transmitted as an electrical output signal to the analyzer device 106 for analysis, for example, directly via conductive leads 108 that extend from the sensor 102 or wirelessly (e.g., via an onboard transmitter/antenna).

In some examples, the sensor 102 may include an exterior layer or coating configured to improve the performance and/or longevity of the sensor 102. For example, the coating may provide waterproof or water-resistant properties to the sensor 102. Preferably, the coating is sufficiently acoustically conductive to allow stress waves to be transmitted and received therethrough while also having limited attenuation and frequency modulation effect, for example, below certain predetermined values. Exemplary but nonlimiting materials for the exterior layer or coating may include polyester and other polymer materials. For certain embodiments in which the sensor 102 includes a polymeric exterior layer or coating, the sensor 102 may be capable of use as both an actuator and a receiver, for example, to measure the Eigen frequencies of the concrete (discussed in detail below).

The form 104 may be any type of structure capable of retaining an uncured concrete mixture to produce a concrete body, for example, a test sample such as a standard test cylinder, or a concrete structure that may form or be part of, as nonlimiting examples, a bridge, pavement, beam, structural member, etc. The form 104 may be a container, a mold, or other structure that includes one or more boundaries that define a cavity for receiving and containing a fresh, uncured concrete mixture. The cavity defined by the boundaries may have various shapes including but not limited to a rectangle, a prism, or a cylinder. In certain embodiments, the form 104 may be an area defined with walls, such as boards or sheets.

In the nonlimiting embodiment of FIG. 1, the form 104 is schematically represented as a hollow cylinder mold of the type commonly used for producing standard test cylinders for concrete testing, generally including a cylindrical wall extending between a first end and a second end wherein at least one of the ends includes or defines an opening to receive the uncured concrete mixture. For convenience, certain examples and embodiments described herein refer to a cylindrical form 104 in use with cement concrete. However, it will be understood that the teachings herein are not limited to any particular shape of the form 104 or to any particular curable material.

In certain embodiments, the sensor 102 may be located within a receptacle 110 that is located within the boundaries of the larger form 104. In such embodiments, the receptacle 110 may be filled with the uncured concrete mixture prior to, after, or simultaneously with the filling of the form 104. The receptacle 110 may be a container, a mold, or other structure that includes one or more boundaries that define a cavity for receiving and containing an uncured concrete mixture. The cavity defined by the boundaries may have various shapes including but not limited to a rectangle, a prism, or a cylinder. The receptacle 110 is preferably configured to be electrically and acoustically insulative.

The receptacle 110 may include one or more layers such as but not limited to an insulation layer and/or a frame layer. The insulation layer may be provided to improve acoustic performance by promoting confinement of stress waves within the receptacle 110 such that the excited structure region is substantially limited inside the receptacle 110 and measured Eigen frequencies provide definite meaning. The insulation layer can be made of various materials which preferably assist in confining the stress waves inside the receptacle 110 while having limited influence on the hydration process of the concrete inside the receptacle 110. A suitable but nonlimiting material for the insulation layer may include a flexible material such as thermally conductive silicone rubber. The receptacle 110 may include an internal sealed pocket of air having a thickness of between about 0.01 to 3 mm for use as the insulation layer or in addition to the insulation layer. If necessary, the frame layer may be provided for additional structural support of the insulation layer. The frame layer may be made of various rigid materials including but not limited to rigid metallic materials, ceramic materials, polymeric materials, and composites.

FIG. 2 represents a nonlimiting example of the receptacle 110 having a cylindrical body that includes a circular sidewall and a base. Distal edges of the cylindrical body define a first opening at a first end of the receptacle 110, and edges of the base define a smaller second opening at a second end of the receptacle 110.

Optionally, the sensor 102 may be embedded in the receptacle 110 such that it is physically isolated from the uncured concrete mixture when the receptacle 110 is filled therewith. In such embodiments, the sensor 102 may be adjacent an acoustically conductive layer of the receptacle 110 such that after filling the receptacle 110 with the uncured concrete mixture, the sensor 102 is in acoustical contact with but not in direct physical contact with the uncured concrete mixture.

The PZT sensor 102 may be located in various positions and orientations within the form 104, though some locations and/or orientations may offer technical advantages over others. In some examples, the receptacle 110 may be used to suspend the PZT sensor 102 in an elevated position within the form 104. The receptacle 110 can include or be coupled to, for example, a string, wire, bracket, receptacle, or other structure that is capable of coupling the sensor 102 to the form 104 or otherwise capable of maintaining the sensor 102 in a specific position within the form 104, preferably prior to, during, and after pouring of the concrete. As a nonlimiting example, in FIGS. 1, 3A-3D, and 4 the receptacle 110 could be utilized to locate the sensor 102 within the cavity of the form 104 in which the uncured concrete mixture is cured to produce the concrete body.

Figure 3A:
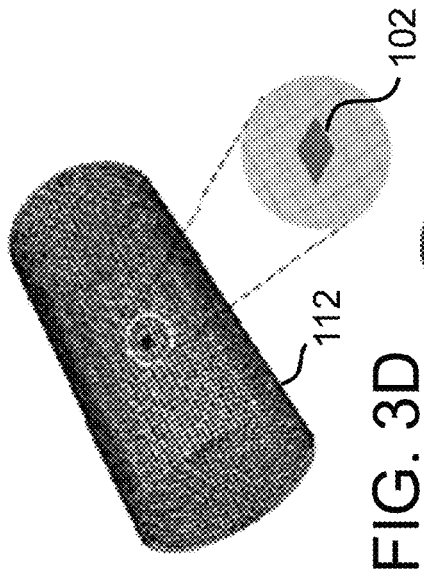
FIGS. 3A, 3B, 3C, and 3D represent various orientations and positions for a sensor of the system of FIG. 1 within a concrete cylinder.
Figure 3B:
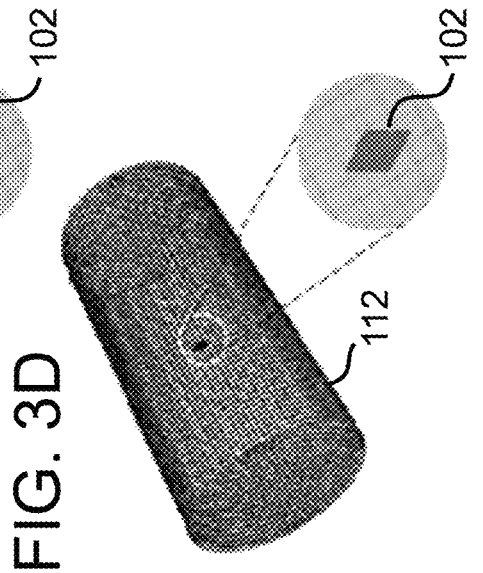
Figure 3C:
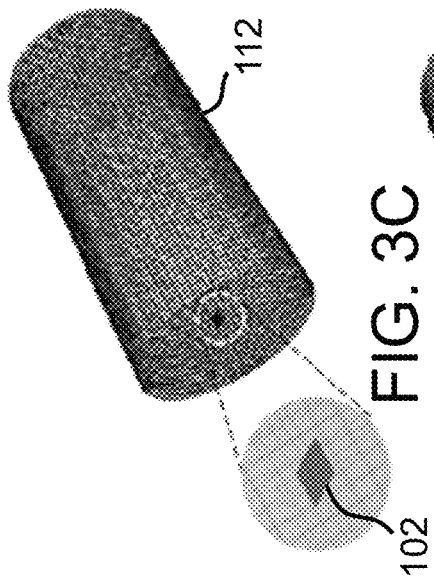
Figure 3D:
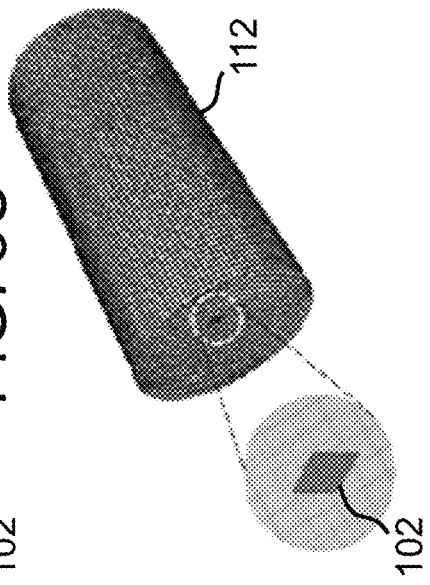

FIGS. 3A through 3D represent examples of various potential orientations and positions for the PZT sensor 102 within a concrete body, schematically represented in FIGS. 3A through 3D as a concrete cylinder 112. For example, the PZT sensor 102 may be oriented perpendicular to faces (i.e., longitudinal ends) of the concrete cylinder 112, as illustrated in FIGS. 3A and 3B. As an alternative example, the PZT sensor 102 may be oriented parallel with the faces of the concrete cylinder 112, as illustrated in FIGS. 3C and 3D. In addition, the PZT sensor 102 may be positioned proximate to one of the faces of the concrete cylinder 112 (FIGS. 3A and 3C) or centrally with respect a length of the concrete cylinder 112 (FIGS. 3B and 3D). As described herein, proximate to a face of the concrete cylinder 112 means a distance not exceeding fifteen percent of the length of the concrete cylinder 112 from the face.

In various experimentations leading to aspects of the present invention, a centrally located PZT sensor 102 with a perpendicular orientation (as in FIG. 3B) was found to have a relatively high resonance amplitude as well as a relatively low interference from undesired modes, making such an orientation and position more accurate than others tested. However, depending on the implementation, lower levels of accuracy may be acceptable, particularly for some benefits available by positioning the PZT sensor 102 closer to one of the faces. For example, positioning the sensor 102 closer to a face may improve the ease of placing the sensor 102 in the form 104. In some examples, the PZT sensor 102 may be placed on an outer surface of an uncured concrete mixture after it is poured into the form 104.

In certain embodiments, the sensor 102 may be positioned within the form 104 or the receptacle 110 in a position corresponding to a predicted maximum or extreme point of a deformation field, a velocity field, or an acceleration field of a certain vibration mode of the concrete body (e.g., concrete cylinder 112) curing therein.

The analyzer device 106 may be a remote computer system that is configured to receive electrical signals produced by the sensor 102 as a result of the piezoelectric effect. Upon receiving the electrical signals from the sensor 102, the analyzer device 106 may execute various logic to analyze the signals to determine material properties of the concrete. For example, the analyzer device 106 may determine one or more resonant frequencies of the concrete based on the electrical signals. As a more specific example, the Young's modulus of the concrete may be determined based on a vibration modal analysis, by which the Young's modulus can be calculated according to measured Eigen frequencies of the concrete within the form 104.

Figure 4:
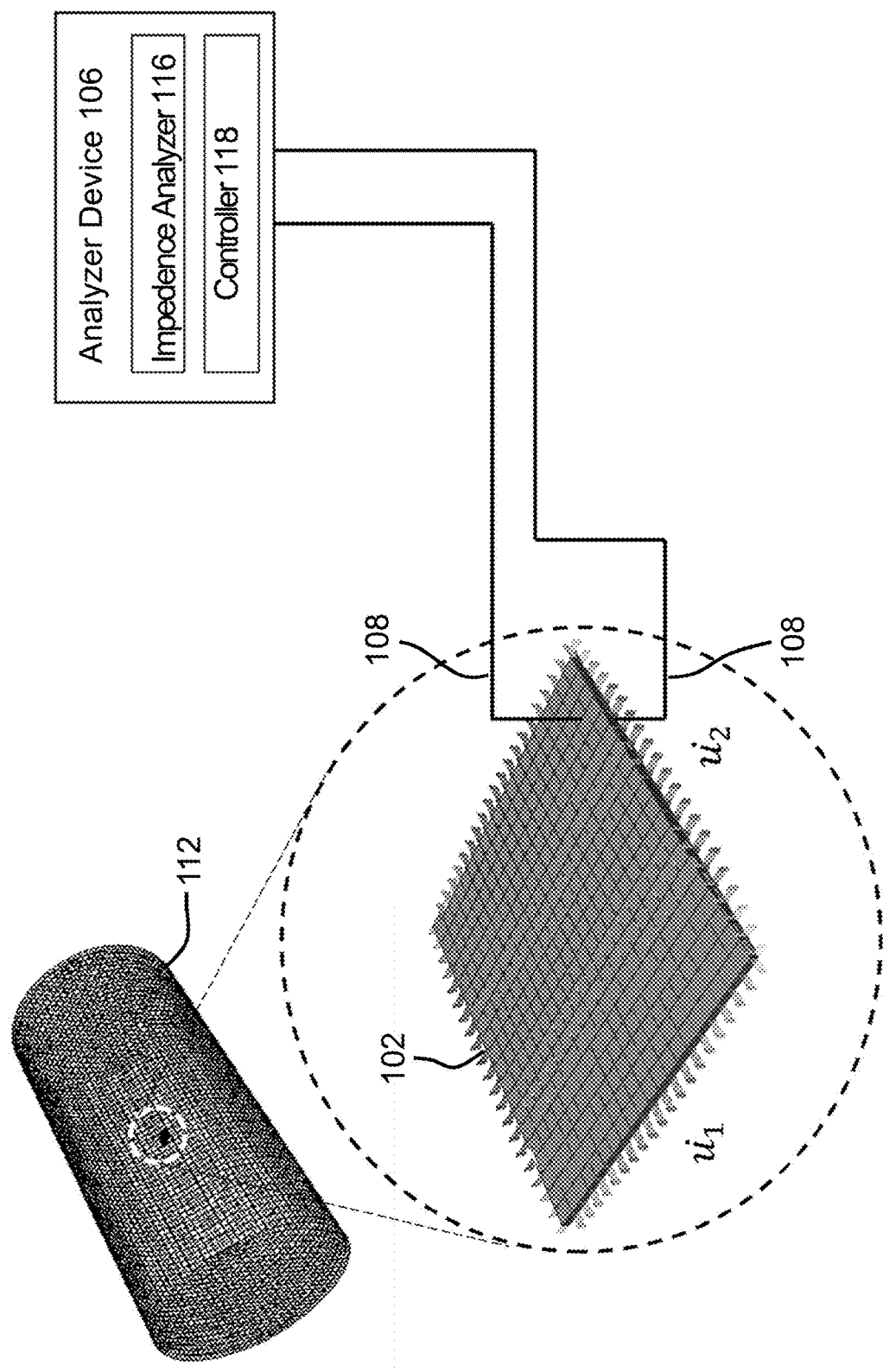
FIGS. 4 and 5 represent additional but optional nonlimiting aspects of the system of FIG. 1.

FIG. 4 represents an example in which the analyzer device 106 includes an impedance analyzer 116 and a controller 118. The impedance analyzer 116 may communicate with the PZT sensor 102 and/or generate an electrical signal-frequency spectrum measurement of the PZT sensor 102. The impedance analyzer 116 and/or controller 118 may identify two or more resonant frequencies of the electrical signal-frequency spectrum measurement. Once the resonant frequencies are identified, the controller 118 may generate the Young's modulus based on the resonant frequencies and the relationship identified in equation 20.

Figure 5:
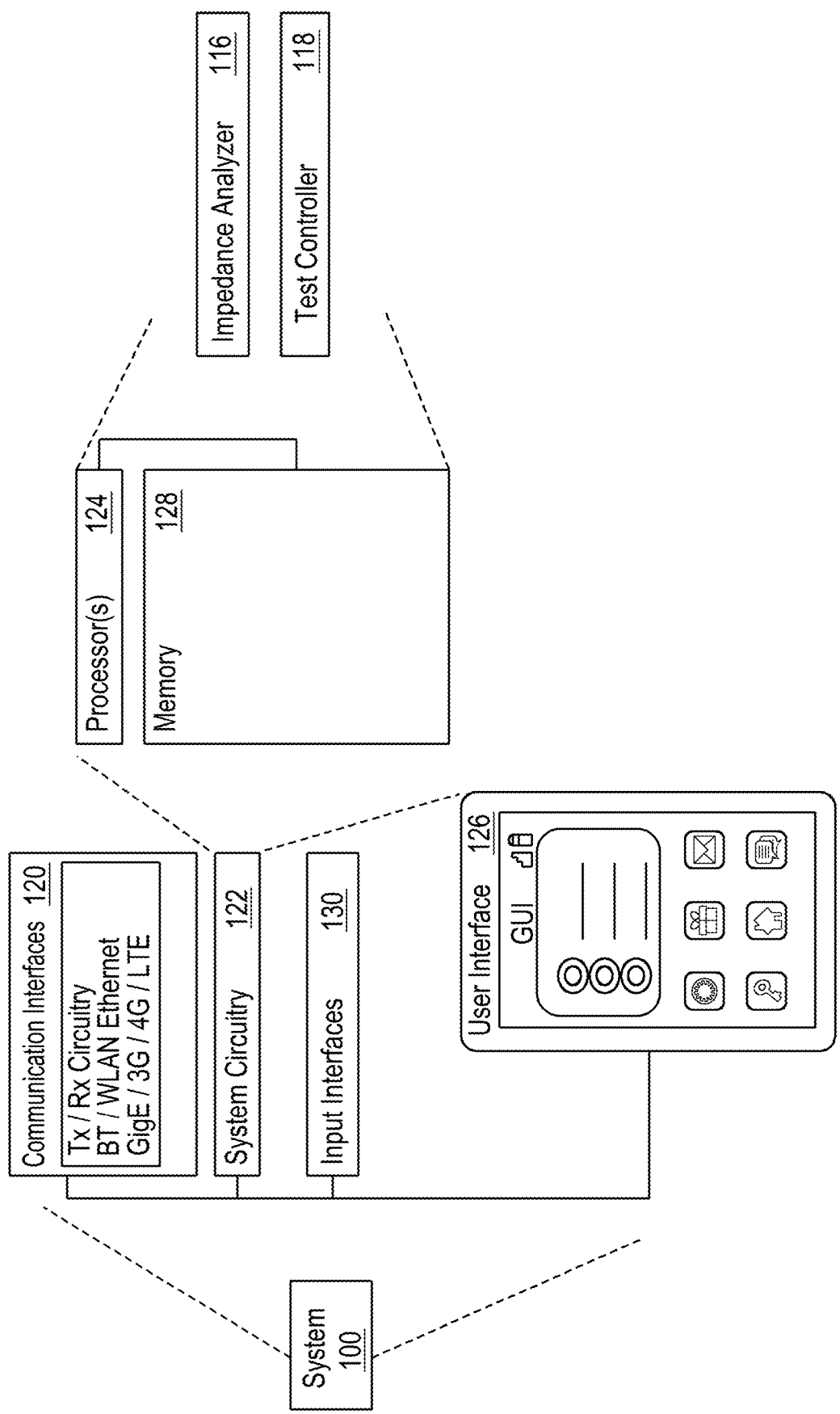

FIG. 5 represents another example in which the system 100 includes communication interfaces 120, input interfaces 130, and/or system circuitry 122. The system circuitry 122 may include one or more processors 124 and/or memory 128. The system 100 may include or be in communication with a user interface 126.

The processor(s) 124 may be in communication with the memory 128. In some examples, the processor(s) 124 may also be in communication with additional elements, such as the communication interfaces 120, the input interfaces 130, and/or the user interface 126. Examples of the processor(s) 124 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor(s) 124 may be one or more devices operable to execute logic. The logic may include computer executable instructions or computer code stored in a non-transient medium such as the memory 128 or in other memory that when executed by the processor 816, cause the processor(s) 124 to perform the operations of the Impedance Analyzer controller, the analyzer device 106, and/or the system 100. The computer code may include instructions executable with the processor(s) 124.

The memory 128 may be any device for storing and retrieving data or any combination thereof. The memory 128 may include non-volatile and/or volatile memory, such as a random-access memory (RAM), a read-only memory (ROM), an erasable programmable read-only memory (EPROM), or flash memory. Alternatively, or in addition, the memory 128 may include an optical, magnetic (hard drive), solid-state drive or any other form of data storage device. The memory 128 may include at least one of the impedance analyzer, the controller, and/or the system 100. Alternatively, or in addition, the memory may include any other component or sub-component of the system 100 described herein.

The user interface 126 may include any interface for displaying graphical information. The system circuitry 122 and/or the communications interface(s) 120 may communicate signals or commands to the user interface 126 that cause the user interface 126 to display graphical information. Alternatively, or in addition, the user interface 126 may be remote to the system 100 and the system circuitry 122 and/or communication interface(s) may communicate instructions, such as HTML, to the user interface 126 to cause the user interface 126 to display, compile, and/or render information content. In some examples, the content displayed by the user interface 126 may be interactive or responsive to user input. For example, the user interface 126 may communicate signals, messages, and/or information back to the communications interface 120 or system circuitry 122.

The system 100 may be implemented in many ways. In some examples, the system 100 may be implemented with one or more logical components. For example, the logical components of the system 100 may be hardware or a combination of hardware and software. The logical components may include the impedance analyzer 116, the controller 118, other components of the analyzer device 106, or any component or subcomponent of the system 100. In some examples, each logic component may include an application specific integrated circuit (ASIC), a field programmable gate array (FPGA), a digital logic circuit, an analog circuit, a combination of discrete circuits, gates, or any other type of hardware or combination thereof. Alternatively, or in addition, each component may include memory hardware, such as a portion of the memory 128, for example, that comprises instructions executable with the processor(s) 124 or other processor to implement one or more of the features of the logical components. When any one of the logical components includes the portion of the memory 128 that comprises instructions executable with the processor(s) 124, the component may or may not include the processor(s) 124. In some examples, each logical component may just be the portion of the memory 128 or other physical memory that comprises instructions executable with the processor(s) 124, or other processor(s), to implement the features of the corresponding component without the component including any other hardware. Because each component includes at least some hardware even when the included hardware comprises software, each component may be interchangeably referred to as a hardware component.

Some features may be stored in a computer readable storage medium (for example, as logic implemented as computer executable instructions or as data structures in memory). All or part of the system 100 and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system 100 may be distributed among multiple entities, such as among multiple processors and memories, optionally including multiple distributed processing systems. Parameters, databases, and other data structures may be separately stored and managed, may be incorporated into a single memory or database, may be logically and physically organized in various ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion herein, regardless of the particular implementation described, is illustrative in nature, rather than limiting. For example, although selected aspects, features, or components of the implementations are depicted as being stored in memory(s), all or part of the system 100 or systems may be stored on, distributed across, or read from other computer readable storage media, for example, secondary storage devices such as hard disks, flash memory drives, floppy disks, and CD-ROMs. Moreover, the various logical units, circuitry and screen display functionality is but one example of such functionality and any other configurations encompassing similar functionality are possible.

The respective logic, software, or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code, and the like, operating alone or in combination. Likewise, processing strategies may include multiprocessing, multitasking, parallel processing, and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, the processor 124 may be implemented as a microprocessor, microcontroller, application specific integrated circuit (ASIC), discrete logic, or a combination of other type of circuits or logic. Similarly, memories may be DRAM, SRAM, Flash, or any other type of memory. Flags, data, databases, tables, entities, and other data structures may be separately stored and managed, may be incorporated into a single memory or database, may be distributed, or may be logically and physically organized in many ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

The system 100 may be implemented with additional, different, or fewer components than illustrated. Each component may include additional, different, or fewer components. With respect to the innovative elements, it should be appreciated that the system 100 may include the form 104 and the sensor 102 without the analyzer device 106. Alternatively, the system 100 may include the analyzer device 106 without the form 104 and the sensor 102. Alternatively, the system 100 may include the analyzer device 106, the form 104, the sensor 102, and/or other components or subcomponents described herein.

Figure 6:
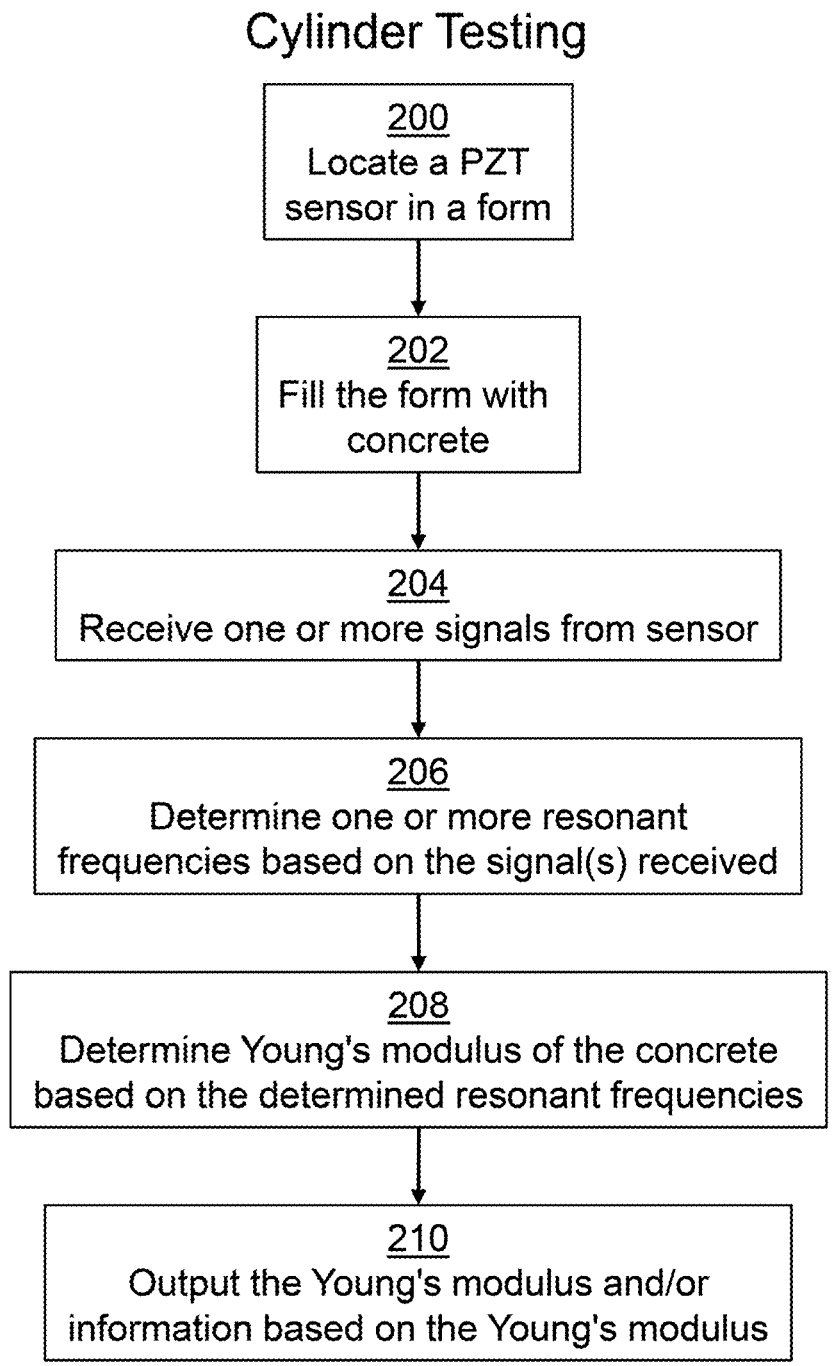
FIGS. 6 and 7 include flow diagrams representing nonlimiting methods for testing concrete with the system of FIGS. 1 through 5.
Figure 7:
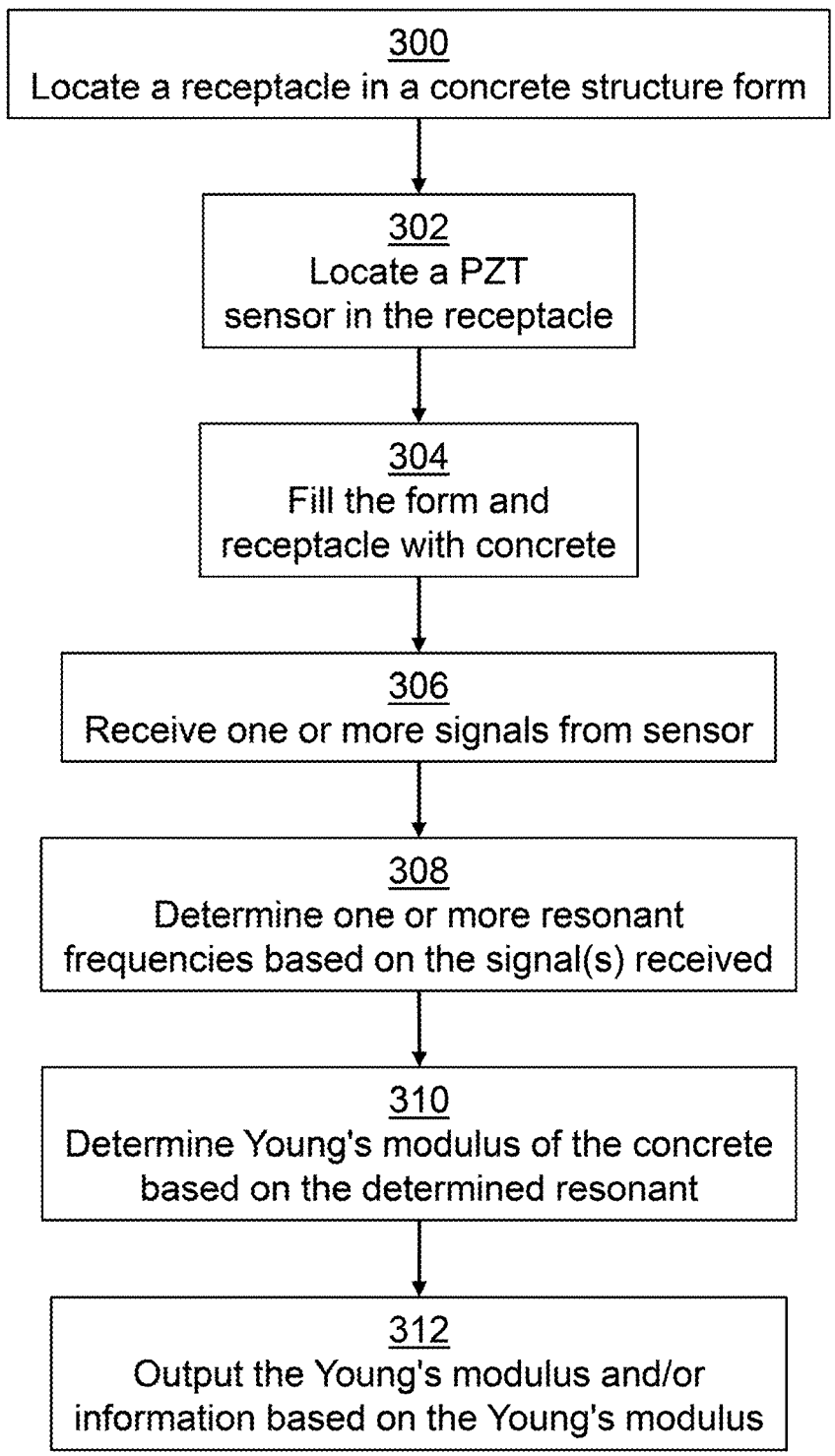

FIGS. 6 and 7 include flow diagrams representing non-limiting methods for testing concrete with the system 100 of FIG. 1. These methods are exemplary, and the steps actually executed may include additional, different, or fewer operations than those illustrated in FIGS. 6 and 7 and may also be executed in a different order than illustrated in FIGS. 6 and 7.

FIG. 6 represents steps of a first method for performing a concrete cylinder test. The method includes locating the PZT sensor 102 within the cavity of the form 104 at step 200. Once the PZT sensor 102 is located and secured, if necessary, in position within the form 104, a fresh uncured concrete mixture may be added to the cavity to fill the form 104 to a desired volume at step 202. In some examples, the form 104 may be partially or entirely filled before insertion of the PZT sensor 102. As the concrete mixture within the form 104 begins the hydration process, a concrete body will be produced in the shape of the cavity with the PZT sensor 102 embedded therein. Vibration within the concrete body caused by the curing process may be converted into an electrical signal by the sensor 102. If present, the conductive leads 108 of the PZT sensor 102 may extend and be exposed from the concrete body to an extent sufficient for use in transmitting the electrical signals therefrom.

The remaining steps 204, 206, 208, and 210 may be performed by a computer system executing computer-executable instructions from a nontransient computer-readable medium. The analyzer device 106 may provide or comprise such computer system to provide the practical applications described herein or may be functionally coupled to and/or in communication with such computer system to provide the electrical signals from the sensor 102 thereto. For convenience of the following discussion, it will be assumed that the analyzer device 106 includes such computer system.

In step 204, the analyzer device 106 receives one or more electrical signals from the sensor 102. In step 206, the analyzer device 106 may determine a first resonant frequency and a second resonant frequency based on the one or more signals received from the PZT sensor 102. The analyzer device 106 may then determine the Young's modulus of the concrete body based on the first and second resonant frequencies at step 208.

Once the Young's modulus of the concrete cylinder has been determined, the analyzer device 106 may output the Young's modulus and/or information based on the Young's modulus at step 210. For example, the analyzer device 106 may determine whether the determined Young's modulus satisfies acceptance criteria. The acceptance criteria may include, for example, a threshold value, and the analyzer device 106 may compare the determined Young's modulus to the threshold value. In some examples, the analyzer device 106 may receive the acceptance criteria via a graphical user interface. In response to the Young's modulus satisfying the acceptance criteria, the analyzer device 106 may output a pass indication. In response to the Young's modulus not satisfying the acceptance criteria, the analyzer device 106 may output a failure indication. Alternatively, or in addition, the analyzer device 106 may output the Young's modulus and/or related information for further analysis.

FIG. 7 represents steps of a second method for performing a material property testing of a concrete body in situ, for example, within a portion of a roadway, sidewalk, foundation, or other structure or object. The method includes locating a receptacle 110 within the cavity of the form 104 at step 300.

In step 302, the PZT sensor 102 may be located and secured, if necessary, in position within the receptacle 110. The fresh uncured concrete mixture may then be added to fill the receptacle 110 and the form 104 to desired volumes at step 304. In some examples, the receptacle 110 may be partially filled before insertion of the PZT sensor 102. As the concrete mixture within the receptacle 110 begins the hydration process, a concrete body will be produced in the shape of the cavity of the receptacle 110 with the PZT sensor 102 embedded therein.

The remaining steps 306, 308, 310, and 312 may be substantially identical or functionally similar as described above in reference to steps 204, 206, 208, and 210, respectively, of the first method represented in FIG. 2 and therefore will not be discussed in detail.

The following description includes certain nonlimiting methods for analyzing the electrical signals produced by the sensor 102. It should be understood that other methods may be implemented to obtain the desired material properties with the system 100 discussed below or to obtain other material properties and information.

In some examples, the analyzer device 106 may determine a first resonant frequency and a second resonant frequency based on an electrical admittance spectrum of the PZT sensor 102. For example, the interaction between the hosting structure (e.g., concrete) and the PZT sensor 102 for a relatively thin planar PZT sensor 102 as represented in FIG. 1 may be represented as discussed below. In particular, the electrical admittance amplitude of the PZT sensor 102 may be expressed as $$\overline{Y} = 4\omega j \frac{l^2}{h}\left[\overline{\varepsilon_{33}^T} - \frac{2d_{31}^2 \overline{Y^E}}{(1-v)} + \frac{2d_{31}^2 \overline{Y^E}}{(1-v)}\left(\frac{Z_{a,eff}}{Z_{a,eff}+Z_{s,eff}}\right)\overline{T}\right] \quad \text{Equation 1}$$

where $\overline{Y}$ is electrical admittance; $\omega$ is the angular frequency; l is half of the PZT length; h is the thickness of PZT; $\overline{\varepsilon_{33}^T} = \varepsilon_{33}^T(1-\sigma j)$ is the complex dielectric permittivity at constant stress; $d_{31}$ is piezoelectric constant; v is the Poisson's ratio of PZT; $\overline{Y^E} = Y^E(1-\eta j)$ is the complex Young's modulus of PZT; $\sigma$ denotes the dielectric loss factor and $\eta$ the mechanical loss factor; $Z_{a,eff}$ and $Z_{s,eff}$ are the effective mechanical impedance of PZT and host structure, respectively;

$$\overline{T} = \frac{\tan C\kappa l}{C\kappa l}$$

is the correction factor, C is constant, $$\kappa = \omega\sqrt{\frac{\rho(1-v^2)}{\overline{Y^E}}}$$

is the wave number of PZT, and $\rho$ is the density of the PZT.

The effective mechanical impedance of free PZT is given by $$Z_{a,eff} = \frac{2h\overline{Y^E}}{j\omega(1-v)\overline{T}} \quad \text{Equation 2}$$

The displacements of the PZT patch in the two principal directions are given by $$u_1 = (A_1 \sin C\kappa x)e^{j\omega t} \quad u_2 = (A_2 \sin C\kappa x)e^{j\omega t} \quad \text{Equation 3}$$

where $A_1$ and $A_2$ are given by $$A_1 + A_2 = \frac{2d_{31}V_0}{(\cos C\kappa l)C\kappa h}\left(\frac{Z_{a,eff}}{Z_{a,eff} + Z_{s,eff}}\right) \quad \text{Equation 4}$$

Assuming the PZT patch vibrates in the same way in two directions, i.e., $A_1=A_2$, and the amplitude of excitation voltage $V_0=1.0$ V, the displacement amplitude of PZT in 1 direction is $$u_1 = \frac{d_{31}\bar{T}l}{h}\left(\frac{Z_{a,eff}}{Z_{a,eff} + Z_{s,eff}}\right) \quad \text{Equation 5}$$

The velocity amplitude of PZT in 1 direction is $$\dot{u}_1 = j\omega u_1 \quad \text{Equation 6}$$

Therefore $$\frac{\partial \dot{u}_1}{\partial \omega} = j \cdot \frac{d_{31}l}{h} \cdot \frac{\partial}{\partial \omega}\left(\frac{\omega \cdot \bar{T} \cdot Z_{a,eff}}{Z_{a,eff} + Z_{s,eff}}\right) \quad \text{Equation 7}$$

The derivative of electrical admittance of PZT to angular frequency is given by $$\frac{\partial \bar{Y}}{\partial \omega} = 4j \cdot \frac{l^2}{h} \cdot \left[\overline{\varepsilon_{33}^T} - \frac{2d_{31}^2\overline{Y^E}}{(1-v)} + \frac{2d_{31}^2\overline{Y^E}}{(1-v)} \cdot \frac{\partial}{\partial \omega}\left(\frac{\omega \cdot \bar{T} \cdot Z_{a,eff}}{Z_{a,eff} + Z_{s,eff}}\right)\right] \quad \text{Equation 8}$$

Equation 7 and Equation 8 can be rewritten as $$\frac{\partial \dot{u}_1}{\partial \omega} = L \cdot \frac{\partial}{\partial \omega}\left(\frac{\omega \cdot \bar{T} \cdot Z_{a,eff}}{Z_{a,eff} + Z_{s,eff}}\right) \quad \text{Equation 9}$$

$$\frac{\partial \bar{Y}}{\partial \omega} = M + N \cdot \frac{\partial}{\partial \omega}\left(\frac{\omega \cdot \bar{T} \cdot Z_{a,eff}}{Z_{a,eff} + Z_{s,eff}}\right) \quad \text{Equation 10}$$

where L, M, N are complex constants.

Comparing Equation 9 and Equation 10, it can be seen that the electrical admittance of PZT has the same resonance behavior as the mechanical vibration of PZT and the resonance is caused by both $Z_{a,eff}$ and $Z_{s,eff}$.

If the frequency of interest is low, i.e., lower than ⅕ of the first resonance frequency of PZT in free boundary condition, the $\bar{T} \approx 1$. Then, Equation 2 can be rewritten as $$Z_{a,eff} = \frac{2h\overline{Y^E}}{j\omega(1-v)} \quad \text{Equation 11}$$

In such condition, $Z_{a,eff}$ has a monotonic relationship with $\omega$ and it does not result in local maximums or minimums in $$\frac{\partial \dot{u}_1}{\partial \omega} \text{ or } \frac{\partial \bar{Y}}{\partial \omega}.$$

The only factor that causes resonance of $\dot{u}_1$ or $\bar{Y}$ is $Z_{s,eff}$, i.e., the mechanical impedance of structure.

Equations 9 through 11 explain why the EMI spectrum can be used to evaluate the velocity spectrum and evaluate the vibration modes of concrete cylinder.

Once the first two resonant frequencies of $\dot{u}_1$ in the low frequency band are extracted from the EMI admittance $\bar{Y}$, the Young's modulus can be calculated according to the same process as the impact resonance (IR) method. The equations are quoted here for convenience.

$$\mu = A_1\left(\frac{f_2}{f_1}\right)^2 + B_1\left(\frac{f_2}{f_1}\right) + C_1 \quad \text{Equation 12}$$

$$A_1 = -8.6457\left(\frac{L}{D}\right)^2 + 24.4431\left(\frac{L}{D}\right) - 12.4778 \quad \text{Equation 13}$$

$$B_1 = 34.5986\left(\frac{L}{D}\right)^2 - 101.7207\left(\frac{L}{D}\right) + 56.172 \quad \text{Equation 14}$$

$$C_1 = -34.6807\left(\frac{L}{D}\right)^2 + 105.979\left(\frac{L}{D}\right) - 62.731 \quad \text{Equation 15}$$

$$A_2 = -0.2792\left(\frac{L}{D}\right)^2 + 1.4585\left(\frac{L}{D}\right) - 2.1093 \quad \text{Equation 16}$$

$$B_2 = 0.0846\left(\frac{L}{D}\right)^2 - 0.5868\left(\frac{L}{D}\right) + 1.3791 \quad \text{Equation 17}$$

$$C_2 = 0.285\left(\frac{L}{D}\right)^2 - 1.7026\left(\frac{L}{D}\right) + 3.3769 \quad \text{Equation 18}$$

$$f_n^1 = A_2(\mu)^2 + B_2(\mu)^2 + C_2 \quad \text{Equation 19}$$

$$E = 2(1+\mu)\rho\left(\frac{2\pi f_1 R_0}{f_n^1}\right)^2 \quad \text{Equation 20}$$

where L is the height of the cylinder; D is the diameter of the cylinder; E, $\mu$, $\rho$ are the Young's modulus, Poisson ratio and density of the concrete, respectively; and $f_1$ and $f_2$ are the first two longitudinal resonant frequencies of the cylinder.

In certain embodiments, a conversion between the determined Young's modulus of the concrete body and the one or more resonant frequencies of the concrete body may be determined using one or more mathematical numerical models. Such mathematical numerical models may include but are not limited to the Rayleigh-Ritz method and the Finite Element method.

While the invention has been described in terms of specific embodiments, it is apparent that other forms could be adopted by one skilled in the art. For example, the physical configuration of the system 100 could differ from that shown, and materials and processes/methods other than those noted could be used. In addition, the invention encompasses additional embodiments in which one or more features or aspects of different disclosed embodiments may be combined. Therefore, the scope of the invention is to be limited only by the following claims.

The invention claimed is:

1. A method comprising:
    locating a piezoelectric sensor within a cavity of a receptacle that is disposed within a cavity of a form, the cavity of the receptacle defined by one or more boundaries;
    fixing the piezoelectric sensor in a predetermined position and orientation within the cavity of the form with the receptacle;
    filling the cavity of the form defined by one or more boundaries with an uncured concrete mixture;
    filling the receptacle with the uncured concrete mixture prior to, after, or simultaneously with the filling of the cavity of the form, wherein the uncured concrete mixture contacts or envelops the piezoelectric sensor within the form;

receiving an electrical signal from the piezoelectric sensor as the uncured concrete mixture cures within the form to define a concrete sample such that the piezoelectric sensor is embedded within the concrete sample;

determining an electrical signal-frequency spectrum of the electrical signal received from the piezoelectric sensor;

determining a resonant frequency of the concrete sample based on the electrical signal-frequency spectrum;

determining a Young's modulus of the concrete sample based on the resonant frequency thereof; and outputting the determined Young's modulus or information based on the determined Young's modulus;

wherein the receptacle is electrically and acoustically insulative such that one or more boundaries of the receptacle reflect and contains stress wave therein and induce resonance of vibrations as the uncured concrete mixture therein cures, and the predetermined position of the piezoelectric sensor is within the receptacle.

2. The method of claim 1, wherein the piezoelectric sensor is embedded within the receptacle, and after filling the receptacle with the uncured concrete mixture the piezoelectric sensor and the uncured concrete mixture are separated by an acoustically conductive layer of the receptacle such that the piezoelectric sensor is in acoustical contact with, but not in direct physical contact the uncured concrete mixture.

3. The method of claim 1, wherein the receptacle includes a thermally conductive silicone rubber.

4. The method of claim 1, wherein the receptacle includes an electrically and acoustically insulative layer that includes a sealed pocket of air having a thickness of between about 0.01 to 3 mm.

5. The method of claim 1, wherein determining the electrical signal-frequency spectrum of the piezoelectric sensor includes analyzing the electrical signal with an impedance analyzer.

6. The method of claim 1, further comprising:
determining a conversion between the determined Young's modulus of the concrete sample and the resonant frequency of the concrete sample using a mathematical numerical model.

7. The method of claim 6, wherein the mathematical numerical model includes at least one of a Rayleigh-Ritz method or a Finite Element method.

8. The method of claim 1, further comprising:
determining whether the Young's modulus satisfies an acceptance criterion;
outputting a pass indication in response to the Young's modulus satisfying the acceptance criterion; and
outputting a failure indication in response to the Young's modulus not satisfying the acceptance criterion.

9. The method of claim 1, further comprising:
protecting the piezoelectric sensor with a waterproof exterior layer, wherein the exterior layer is sufficiently acoustically conductive to allow stress waves to be transmitted and received therethrough with attenuation and frequency modulation below predetermined values.

10. The method of claim 9, further comprising curing the uncured concrete mixture to produce a concrete body.

11. The method of claim 1, further comprising positioning the piezoelectric sensor at an extreme point of a deformation field, a velocity field, or an acceleration field of a certain vibration mode of the concrete sample inside the form.

12. A method comprising:
filling a cavity of a form defined by one or more boundaries with an uncured concrete mixture such that the uncured concrete mixture contacts or envelops a piezoelectric sensor within the form;
receiving an electrical signal from the piezoelectric sensor as the uncured concrete mixture cures within the form to define a concrete sample, the piezoelectric sensor positioned at an extreme point of a deformation field, a velocity field, or an acceleration field of a certain vibration mode of the concrete sample inside the form;
determining an electrical signal-frequency spectrum of the electrical signal received from the piezoelectric sensor;
determining a resonant frequency of the concrete sample based on the electrical signal-frequency spectrum;
determining a Young's modulus of the concrete sample based on the resonant frequency thereof; and
outputting the determined Young's modulus or information based on the determined Young's modulus.

13. The method of claim 12, further comprising:
disposing the piezoelectric sensor within a cavity of a receptacle, the cavity of the receptacle defined by a boundary; and
fixing the piezoelectric sensor in a predetermined position and orientation within the cavity of the form with the receptacle.

14. The method of claim 13, further comprising:
filling the cavity of the receptacle with the uncured concrete mixture prior to, after, or simultaneously with the filling of the cavity of the form.

15. The method of claim 14, wherein the receptacle is electrically and acoustically insulative such that the boundary of the receptacle reflects and contains stress waves therein and induces a resonance of vibrations as the uncured concrete mixture therein cures.

16. The method of claim 14, wherein after filling the cavity of the receptacle with the uncured concrete mixture, the piezoelectric sensor and the uncured concrete mixture are separated by an acoustically conductive layer of the receptacle such that the piezoelectric sensor is in acoustical contact with, but not in direct physical contact with, the uncured concrete mixture.

17. The method of claim 13, wherein the receptacle includes a thermally conductive silicone rubber.

18. The method of claim 13, wherein the receptacle includes an electrically and acoustically insulative layer that includes a sealed pocket of air having a thickness in a range of about 0.01 mm to about 3 mm.

19. The method of claim 12, further comprising:
determining whether the Young's modulus satisfies an acceptance criterion;
outputting a pass indication in response to the Young's modulus satisfying the acceptance criterion; and
outputting a failure indication in response to the Young's modulus not satisfying the acceptance criterion.

20. The method of claim 12, further comprising:
determining a conversion between the determined Young's modulus of the concrete sample and the resonant frequency of the concrete sample using a mathematical numerical model, the mathematical numerical model including at least one of a Rayleigh-Ritz method or a Finite Element method.

* * * * *